(12) United States Patent
Groves et al.

(10) Patent No.: US 10,590,057 B2
(45) Date of Patent: Mar. 17, 2020

(54) ISOTOPIC FLUORINATION AND APPLICATIONS THEREOF

(71) Applicant: THE TRUSTEES OF PRINCETON UNIVERSITY, Princeton, NJ (US)

(72) Inventors: John T. Groves, Princeton, NJ (US); Xinyi Chen, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 16/060,665

(22) PCT Filed: Dec. 14, 2016

(86) PCT No.: PCT/US2016/066648
§ 371 (c)(1),
(2) Date: Jun. 8, 2018

(87) PCT Pub. No.: WO2017/106340
PCT Pub. Date: Jun. 22, 2017

(65) Prior Publication Data
US 2018/0362432 A1    Dec. 20, 2018

Related U.S. Application Data

(60) Provisional application No. 62/267,097, filed on Dec. 14, 2015.

(51) Int. Cl.
*C07C 17/10*    (2006.01)
*C07C 17/12*    (2006.01)
(Continued)

(52) U.S. Cl.
CPC .......... *C07C 45/63* (2013.01); *B01J 31/1815* (2013.01); *B01J 31/22* (2013.01); *B01J 31/2256* (2013.01); *B01J 31/32* (2013.01);

*C07B 39/00* (2013.01); *C07B 59/00* (2013.01); *C07C 17/14* (2013.01); *C07C 67/287* (2013.01); *C07C 67/307* (2013.01); *C07C 231/12* (2013.01); *C07C 253/30* (2013.01); *C07C 269/06* (2013.01); *C07D 209/48* (2013.01); *C07D 209/50* (2013.01); *C07F 13/005* (2013.01);
(Continued)

(58) Field of Classification Search
CPC .......... C07C 17/10; C07C 17/12; C07C 17/14
See application file for complete search history.

(56) References Cited

U.S. PATENT DOCUMENTS

2014/0227184 A1    8/2014    Groves et al.

FOREIGN PATENT DOCUMENTS

WO    20150134467 A1    9/2015

OTHER PUBLICATIONS

International Search Report and Written Opinion corresponding to PCT/US2016/066648, dated Feb. 17, 2017, 8 pages.
(Continued)

*Primary Examiner* — Medhanit W Bahta
(74) *Attorney, Agent, or Firm* — J. Clinton Wimbish; Nexsen Pruet, PLLC

(57) ABSTRACT

Methods of C—H bond fluorination using non-heme manganese catalyst are described herein. For example, a method comprises providing a reaction mixture including a non-heme manganese catalyst, a substrate comprising an sp³ C—H bond and a fluorinating agent and converting the sp³ C—H bond to a C—F bond in the presence of the non-heme manganese catalyst or a derivative thereof.

25 Claims, 9 Drawing Sheets

(51) Int. Cl.
| | |
|---|---|
| C07C 17/14 | (2006.01) |
| C07C 45/63 | (2006.01) |
| C07C 67/287 | (2006.01) |
| C07C 253/30 | (2006.01) |
| B01J 31/22 | (2006.01) |
| C07B 59/00 | (2006.01) |
| C07D 209/48 | (2006.01) |
| B01J 31/32 | (2006.01) |
| C07C 67/307 | (2006.01) |
| C07C 231/12 | (2006.01) |
| C07C 269/06 | (2006.01) |
| C07B 39/00 | (2006.01) |
| B01J 31/18 | (2006.01) |
| C07D 209/50 | (2006.01) |
| C07F 13/00 | (2006.01) |

(52) U.S. Cl.
CPC .... *B01J 2231/40* (2013.01); *B01J 2531/0238* (2013.01); *B01J 2531/72* (2013.01); *C07B 2200/05* (2013.01); *C07C 2601/18* (2017.05); *C07C 2602/08* (2017.05); *C07C 2602/10* (2017.05); *C07C 2603/32* (2017.05)

(56) References Cited

OTHER PUBLICATIONS

Cusso, O. et al., Highly stereoselective epoxidation with H2O2 catalyzed by electron-rich aminopyridine manganese catalysts, Organic Letters, 2013, vol. 15, No. 24, 4 pages.

Nehru, K. et al., A highly efficient non-heme manganese complex in oxygenation reactions, Chemical Communications, 2007, vol. 44, pp. 4623-4625.

Wu, X. et al., A highly reactive mononuclear non-I leme manganese (IV)-oxo complex that can activate the strong C-H bonds of alkanes, Journal of the American Chemical Society, 2011, vol. 133, No. 50, pp. 20088-20001.

Murphy, A. et al., Efficient epoxidation of electron-deficient olefins with a cationic manganese complex, Journal of the American Chemical Society, 2003, vol. 125, No. 18, pp. 5250-5251.

US 10,590,057 B2

ISOTOPIC FLUORINATION AND APPLICATIONS THEREOF

RELATED APPLICATION DATA

This application is a U.S. National Phase of PCT/US2016/066648, filed Dec. 14, 2016, which claims priority pursuant to 35 U.S.C. § 119(e) to U.S. Provisional Patent Application Ser. No. 62/267,097 filed Dec. 14, 2015, each of which is incorporated herein by reference in its entirety.

STATEMENT OF GOVERNMENT RIGHTS

This invention was made with government support under Grant No. CHE-1148597 awarded by the National Science Foundation. The government has certain rights in the invention.

FIELD

The present invention relates to C—H bond fluorination and, in particular, to fluorination of aliphatic C—H bonds with fluorine isotope via non-heme manganese catalyst.

BACKGROUND

Positron emission tomography (PET) is a noninvasive and highly sensitive imaging technology for quantitative measurement in the picomolar range and visualization of biological interactions in vivo at the molecular level. Several positron-emitting radioisotopes can be incorporated into biomolecules, but the most prominent radionuclide in the clinic is fluorine-18 ($^{18}$F). By far [$^{18}$F]fluorodeoxyglucose ([$^{18}$F]FDG), the most successful commercial PET radiopharmaceutical, has prevailed in oncological diagnosis over two decades.

However, this molecular imaging modality is far from fully exploited, mainly because chemical reactions to introduce $^{18}$F atom into radiotracer candidates are limited. In addition to the difficulty in C—F bond formation, short half-life of $^{18}$F (~110 min), low $^{18}$F concentration as well as solvent compatibility exacerbate the development of $^{18}$F labeling methodology. Typically, most of radiotracers are labeled through nucleophilic $^{18}$F substitution, in which harsh reaction conditions are required and therefore, functional group compatibility is diminished. Recently, a number of novel $^{18}$F labeling strategies have been developed that can incorporate $^{18}$F into molecules of increasing complexity. Some of these methods have been scaled up and demonstrated in image applications with high specify activity.

Nevertheless, most of current $^{18}$F labeling methods follow "preinstallation" strategy, in which a reactive functional group is preinstalled at the proposed labeled site and subsequently substituted by $^{18}$F. Additional synthetic steps to prepared reactive precursors and harsh reaction conditions of $^{18}$F labeling step limit the application into a broad substrate scope.

SUMMARY

In view of these synthetic challenges, methods of C—H bond fluorination are described herein, including C-$^{18}$F bond formation using non-heme manganese catalyst. Briefly, a method comprises providing a reaction mixture including a non-heme manganese catalyst, a substrate comprising an sp$^3$ C—H bond and a fluorinating agent and converting the sp$^3$ C—H bond to an sp$^3$ C—F bond in the presence of the non-heme manganese catalyst or derivative thereof. In some embodiments, the fluorinating agent is an $^{18}$F source, wherein the C—H bond is converted to a C-$^{18}$F bond. The $^{18}$F source is no carrier added [$^{18}$F]F$^-$, in some embodiments. As described further herein, fluorine can be transferred to the substrate from an equatorial ligand position on the non-heme manganese catalyst. Moreover, fluorination and isotopic labeling methods described herein are compatible with a number of functionalities. Suitable substrates, for example, can include one or more functionalities selected from the group consisting of ester, ether, ketone, cyanide, imide, aryl halide and alkyl halide. Such compatibility can permit late stage labeling of a number of organic compounds, including various pharmaceutical compounds.

In further embodiments, non-aliphatic C—H bonds, such as benzylic C—H bonds, can also undergo fluorination according to methods described herein.

These and other embodiments are further described in the following detailed description.

DETAILED DESCRIPTION

Figure 1:
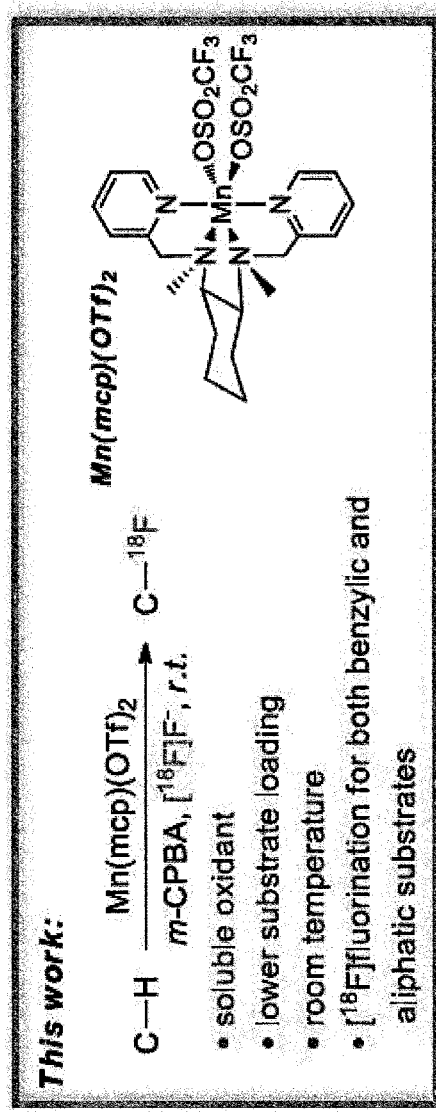
FIG. 1 illustrates C—H [$^{18}$F] fluorination according to some embodiments described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

DEFINITIONS

The term "alkyl" as used herein, alone or in combination, refers to a straight or branched saturated hydrocarbon group. For example, an alkyl can be $C_1$-$C_{30}$.

The term "alkenyl" as used herein, alone or in combination, refers to a straight or branched chain hydrocarbon group having at least one carbon-carbon double bond.

The term "aryl" as used herein, alone or in combination, refers to an aromatic monocyclic or multicyclic ring system optionally substituted with one or more ring substituents The term "heteroaryl" as used herein, alone or in combination, refers to an aromatic monocyclic or multicyclic ring system in which one or more of the ring atoms is an element other than carbon, such as nitrogen, oxygen and/or sulfur.

The term "cycloalkyl" as used herein, alone or in combination, refers to a non-aromatic, saturated mono- or multicyclic ring system optionally substituted with one or more ring substituents.

The term "cycloalkenyl" as used herein, alone or in combination, refers to a non-aromatic, mono- or multicyclic ring system having at least one carbon-carbon double bond and is optionally substituted with one or more ring substituents.

Methods of C—H bond fluorination comprise providing a reaction mixture including a non-heme manganese catalyst, a substrate comprising an sp³ C—H bond and a fluorinating agent and converting the sp³ C—H bond to an sp³ C—F bond in the presence of the non-heme manganese catalyst or derivative thereof. In some embodiments, the fluorinating agent is an $^{18}$F source, wherein the C—H bond is converted to C-$^{18}$F. In some embodiments, fluorine can be transferred to the substrate from an equatorial ligand position on the non-heme manganese catalyst.

Turning now to specific components, the non-heme manganese catalyst can employ a variety of ligands. The non-heme manganese catalyst, in some embodiments, comprises at least one bidentate or polydentate ligand. The non-heme manganese catalyst also comprises one or more equatorial ligands operable to be displaced by fluorine. Displacement by fluorine can occur in the reaction mixture. Equatorial fluorine transfer to the substrate is a fundamentally different approach compared to prior manganese catalyst employing porphyrin or salen (N,N-bis(salicyaldehyde)ethylenediimine) ligand-based architectures. Porphyrin and salen ligands occupy the four equatorial sites of the manganese complex, thereby precluding equatorial fluorine. In such manganese complexes, fluorine ligand resides at one or both axial positions prior to substrate transfer.

Manganese catalyst of methods described herein, in some embodiments, is of formula (I):

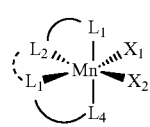

Figure 3:
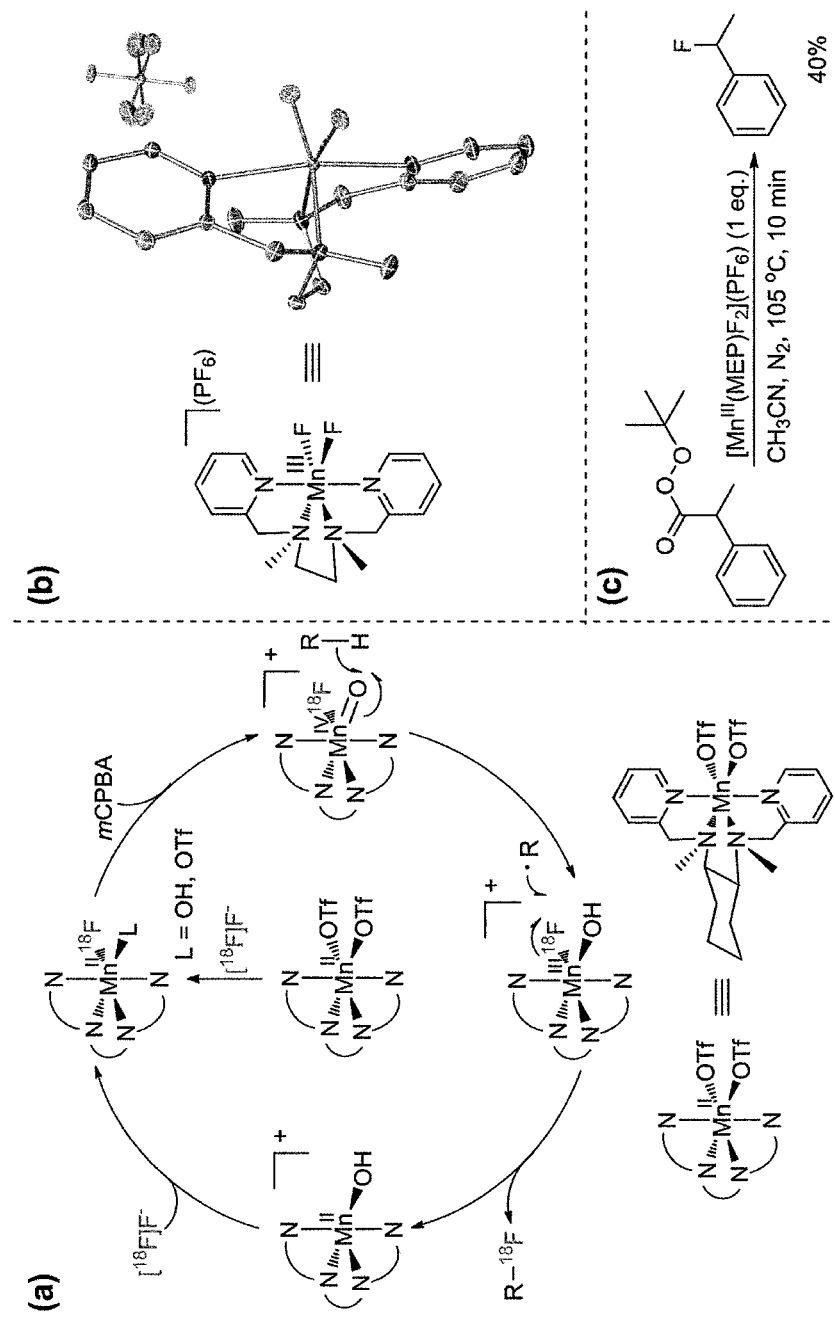
FIG. 3(a) illustrates a proposed catalytic cycle for non-heme manganese catalyzed C—H [$^{18}$F] fluorination described herein.
FIG. 3(b) illustrates the crystal structure of non-heme cis-difluoroMn$^{III}$ complex [Mn$^{III}$(mep)F$_2$](PF$_6$).
FIG. 3(c) illustrates a reactivity study of [Mn$^{III}$(mep)F$_2$](PF$_6$).

(I)

wherein $L_1$ and $L_2$ form a first bidentate ligand and $L_3$ and $L_4$ form a second bidentate ligand optionally bound to the first bidentate ligand. In some embodiments, $X_1$ and $X_2$ are independently selected from the group consisting of fluorine, hydroxyl (OH), oxo (O), triflate (OTf), mesylate (OMs) and tosylate (OTs). Table I below provides various manganese catalytic species of formula (I) according to some non-limiting embodiments. As set forth herein, catalytic species listed in Table I can exist at one or more points in the catalytic fluorination cycle. Species of Table I can exist as starting catalytic reagent or catalytic intermediates. Depending on fluorination reaction parameters, $X_1$ and $X_2$ can be the same or different. In some embodiments, $X_1$ and $X_2$ are both fluorine. In other embodiments, $X_1$ can be fluorine with $X_2$ being hydroxyl or oxo ligand. As discussed further herein $X_1$ and $X_2$ can initially comprise ligands displaceable by fluorine and/or other species in the reaction mixture. For example, $X_1$ and $X_2$ can be independently selected from the group consisting of substituted sulfonate compounds including triflate (OTf), mesylate (OMs) and tosylate (OTs). Fluorinating agent in the reaction mixture can displace $X_1$ or $X_2$ during the catalytic cycle as illustrated in FIG. 3(a).

Figure 2:
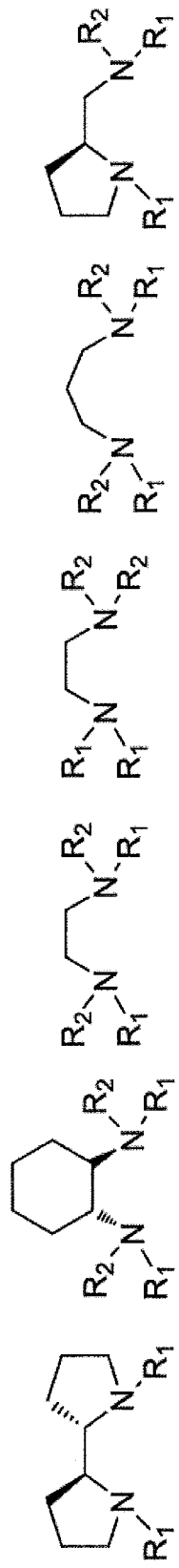
FIG. 2 illustrates various ligand options for non-heme manganese catalyst described herein.
Figure 2:
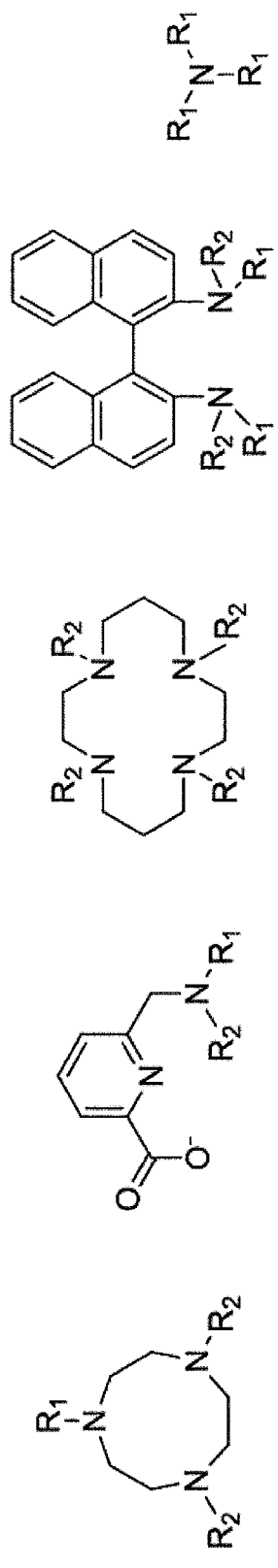
Figure 2:
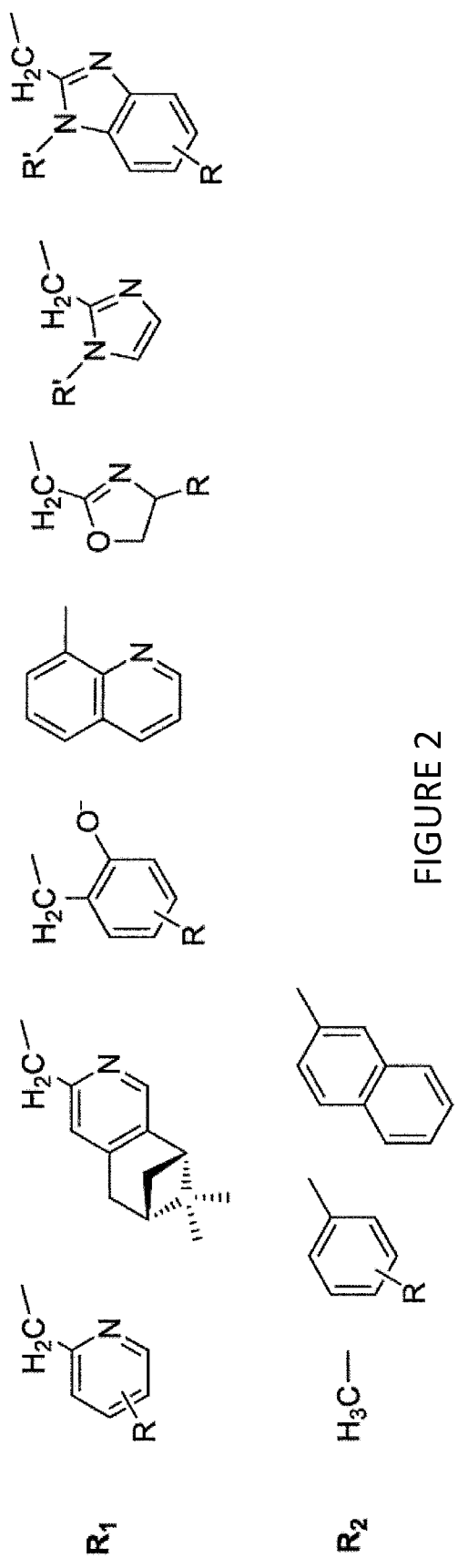

As indicated by the dashed bond in formula (I), $L_1$-$L_4$ can combine to form a tetradentate ligand, such as N,N'-dimethyl-N,N-bis(2-pyridylmethyl)cyclohexane-trans-1,2-diamine (mcp), (N,N'-dimethyl-N,N'-bis-(2-pyridyl methyl)-ethane-1,2-diamine) (mep) or 2-((2-[1-(pyridine-2-ylmethyl)pyrrolidin-1-yl)methyl)pyridine) (pdp) or derivatives thereof. Coordinating atoms of $L_1$-$L_4$ can be nitrogen, oxygen, carbon or various combinations thereof. In some embodiments, coordinating atoms of $L_1$-$L_4$ are part of aromatic ring moieties. Alternatively, coordinating atoms of $L_1$-$L_4$ are part of alkyl, cycloalkyl, alkenyl or cycloalkenyl moieties. FIG. 2 illustrates various non-limiting ligand options for $L_1$-$L_4$ of manganese catalyst described herein.

TABLE I

| Non-Heme Mn Catalytic Species |
|---|
| Mn(mep)F₂ |
| Mn(mcp)(OTf)₂ |
| Mn(mcp)(OH)(F) |
| Mn(mcp)(O)(F) |
| Mn(pdp)(OTf)₂ |
| Mn(pdp)(OH)(F) |
| Mn(pdp)(O)(F) |

Non-heme manganese catalyst can be added to the reaction mixture in any amount not inconsistent with the objectives of the present invention. In some embodiments, non-heme manganese catalyst is present in the reaction mixture in an amount of 0.5-30 mol %. Non-heme manganese catalyst may also be present in the reaction mixture in amounts selected from Table II.

TABLE II

| Non-Heme Manganese Catalyst (mol %) |
|---|
| 1-25 |
| 5-25 |
| 10-20 |
| 1-15 |
| 15-30 |

In addition to manganese catalyst, the reaction mixture includes substrate comprising one or more sp³ C—H bonds. Various substrates having sp³ C—H bonds can be directly fluorinated according to methods descried herein. As illustrated in the examples below, the C—H bond participating in fluorination can be part of an acyclic alkyl moiety or cyclic alkyl moiety. Fluorinated acyclic or cyclic alkyl moieties can be coupled to aryl and/or heteroaryl moieties in some embodiments. Fluorination methods described herein are also compatible with a number of functionalities. Suitable substrates, for example, can include one or more functionalities selected from the group consisting of ester, ether, ketone, cyanide, imide, aryl halide and alkyl halide. Such compatibility can permit late stage labeling of a number of organic compounds, including various pharmaceutical compounds and common scaffolds in bioactive molecules including, but not limited to, amino acids, indan, dibenzocycloheptene and tetrahydronaphthalene. Compounds of Table III and FIGS. 6 and 7 herein illustrate the diversity of suitable substrates for fluorination.

TABLE III

| $^{18}$F Labeled Biocative Compounds |
|---|
| $^{18}$F-celestolide |
| $^{18}$F-protected fingolimod |
| $^{18}$F-N-TFA-rasagiline |
| $^{18}$F-ibuprofen ester |
| $^{18}$F-protected dopamine |
| $^{18}$F-N-Phth-amantadine |

Any fluorinating agent not inconsistent with the objectives of the present invention can be used in the reaction mixture. In some embodiments, for example, silver fluoride (AgF) or silver fluoride/trimethylamine trihydrofluoride is the fluorinating agent. Fluorinating agent can also provide $^{18}$F for isotopic labeling applications. Any $^{18}$F source compatible with direct C—H fluorination in conjunction with non-heme manganese catalyst described herein can be used. In some embodiments, the source is fluoride ion, [$^{18}$F]F$^-$. Such fluoride ion sources can be provided as alkali metal compounds including K[$^{18}$F]F. Moreover, $^{18}$F sources can be no carrier added.

Additional components of the reaction mixture can include oxidant. Any oxidant compatible with C—H fluorination described herein can be used. In some embodiments, the oxidant is soluble in the reaction mixture. For example, meta-chloroperoxybenzoic acid (m-CPBA) can be used as soluble oxidant in acetone and acetonitrile solvent systems. Oxidant may participate in the catalytic cycle by oxidizing the non-heme manganese catalyst to afford a reactive oxo-Mn(IV) intermediate which subsequently abstract a H atom from the substrate, producing a carbon centered radical and cis-$^{18}$F-Mn$^{II}$—OH rebound species.

As detailed in the examples herein, phase transfer catalyst may be absent in the reaction mixture. Examples of phase transfer catalyst absent from the reaction mixture include but are not limited to tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

Methods described herein can provide labeled compound in generally good yield. For $^{18}$F labeling, a method can have a radiochemical conversion (RCC) selected from Table IV.

TABLE IV

| Radiochemical Conversion |
|---|
| ≥30 |
| ≥40 |
| ≥50 |
| ≥60 |
| ≥70 |
| 30-90 |

Given the foregoing radiochemical conversions, less substrate loadings are achievable relative to prior $^{18}$F methods. Prior fluorination methods with Mn(salen) complexes, for example, can require substrate loadings at least five times greater than those for non-heme manganese catalytic species described herein. Fluorine transfer to the substrate via equatorial ligand position on the non-heme manganese catalyst may facilitate fluorination efficiencies and marks a fundamental mechanistic departure from prior manganese catalytic species wherein fluorine transfer to the substrate occurs from an axial position on the Mn complex.

While not wishing to be bound by any theory, a proposed catalytic cycle for non-heme manganese catalyzed C—H [$^{18}$F] fluorination is illustrated in FIG. 3(a). Due to limiting amount of [$^{18}$F]fluoride in this reaction condition, the resting state of the catalyst is likely to be a cis-$^{18}$F-Mn$^{II}$—OH species. m-CPBA oxidizes the resting Mn$^{II}$ catalyst to afford a reactive oxo-Mn(IV) intermediate, which subsequently abstracts a H atom from the substrate, producing a carbon-centered radical and a cis-$^{18}$F-Mn$^{IV}$—OH rebound species. The $^{18}$F-labeled product is formed via the [$^{18}$F]fluorine transfer from cis-$^{18}$F-Mn$^{IV}$—OH complex to substrate radical, together with the regeneration of the resting Mn$^{II}$ catalyst.

Several preliminary experiments were conducted to examine this mechanistic hypothesis. 66% of [$^{18}$F] Fluoride loaded on an anion exchange cartridge could be released using the catalyst in acetone solution, suggesting a ligand exchange proceeded during the elution. Treating Mn$^{II}$(mcp)(OTf)$_2$ with m-CPBA in acetonitrile at −30° C., a high valent oxomanganese species was generated, indicated by the appearance of a broad absorption from 600 nm to 1100 nm at UV-Vis spectra. The EPR spectrum of this manganese complex showed a typical high-valent mononuclear Mn$^{IV}$ species. These results were assigned to the formation of an oxo-Mn$^{IV}$ complex and it is likely that this species mediates the hydrogen abstraction. This postulate was further supported by measurement of the deuterium kinetic isotope effect (KIE). An intermolecular competitive KIE of 2.7 was observed with a 1:1 mixture of cyclooctane and cyclooctane-d$_{16}$, which is similar with the KIE value of hydrogen abstraction by reported non-heme mononuclear oxo-Mn$^{IV}$ species.

The key step in forming a $^{18}$F-labeled product can be the [$^{18}$F]fluorine delivery process from cis-$^{18}$F-Mn$^{IV}$—OH species to carbon radical. Even though a trans-difluoroMn$^{IV}$ porphyrin was isolated and proved to have fluorine transfer ability, there is no example for such a F atom transfer from a non-heme species. A non-heme cis-difluoroMn$^{III}$ complex [Mn$^{III}$(mep)F$_2$](PF$_6$) (mep is N,N'-dimethyl-N,N'-bis-(2-pyridyl methyl)-ethane-1,2-diamine) was isolated and characterized. This Mn$^{III}$ complex was obtained by treating mep ligand with MnF$_3$ and then introducing KPF$_6$ for precipitation. The crystal structure of this complex (FIG. 3, b) showed the manganese ion is coordinated by two fluorides that are in cis positions one to the other. The Mn$^{III}$—F bond lengths of 1.8172(7) Å and 1.8214(7) Å are close to other structure characterized non-heme fluoro-Mn$^{III}$ species. It was found that in the presence of stoichiometric amounts of [Mn$^{III}$(mep)F$_2$](PF$_6$), phenyl ethyl radical generated by the thermal decomposition of tert-butyl 2-phenylpropaneperoxoate, a 40% yield of 1-fluoroethylbenzene was obtained. This result demonstrates that non-theme fluoroMn$^{III}$ species can trap the radical and deliver the fluorine atom.

Figure 4:
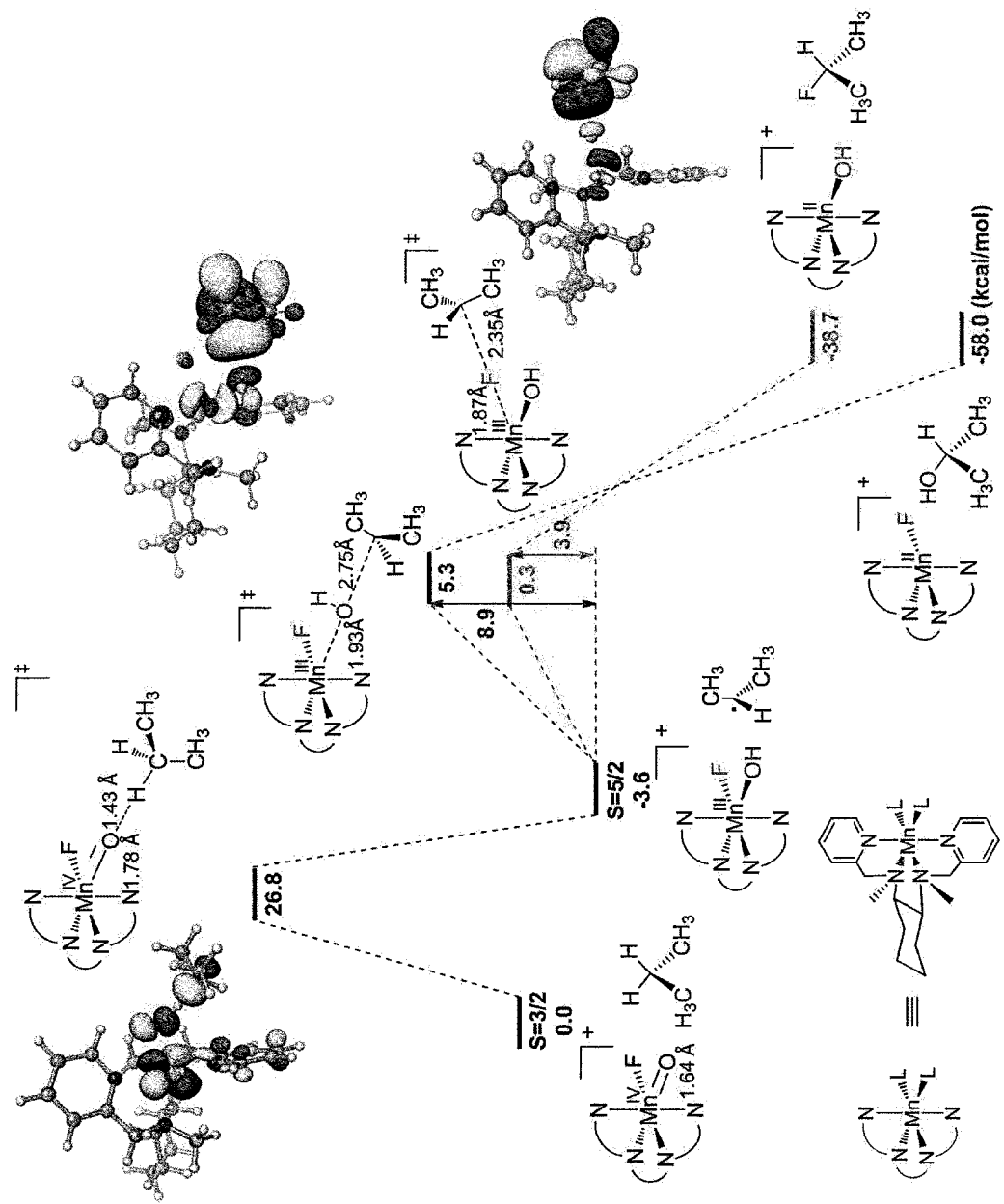
FIG. 4 illustrates DFT calculations of potential energy surface for hydrogen abstraction, fluorine rebound and oxygen rebound steps.

Density functional theory (DFT) calculations were used to explore the potential energy and electronic structure of intermediates and transition states proposed in FIG. 4 in an acetone solvent continuum. The activation energy of H abstraction of the secondary hydrogen in isopropane by [Mn$^{IV}$(O)(F)(mcp)]$^-$ is 26.8 kcal/mol. F atom transfer from [Mn$^{III}$(OH)(F)(mcp)]$^-$ to the isopropyl radical was predicted to occur with a low activation barrier of 3.9 kcal/mol. A higher calculated transition state was landed for the OH rebound, implicating that a faster reaction rate for F rebound. This is consistent with the fact that $^{18}$F labeling was observed even though the concentration of [$^{18}$F]fluoride is very low in reaction mixture.

These and other embodiments are further illustrated by the following non-limiting examples.

Example 1—Radiosynthesis of $^{18}$F Labeled Molecules

Figure 5:
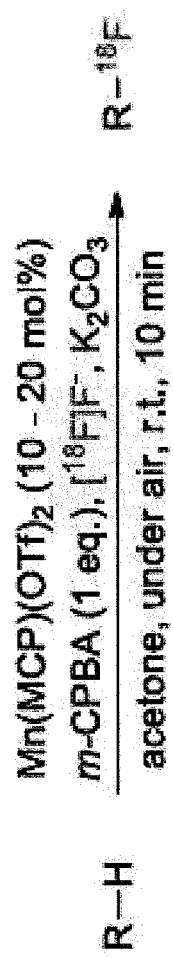
FIG. 5 illustrates C—H [$^{18}$F] fluorination according to some embodiments described herein.
Figure 6:
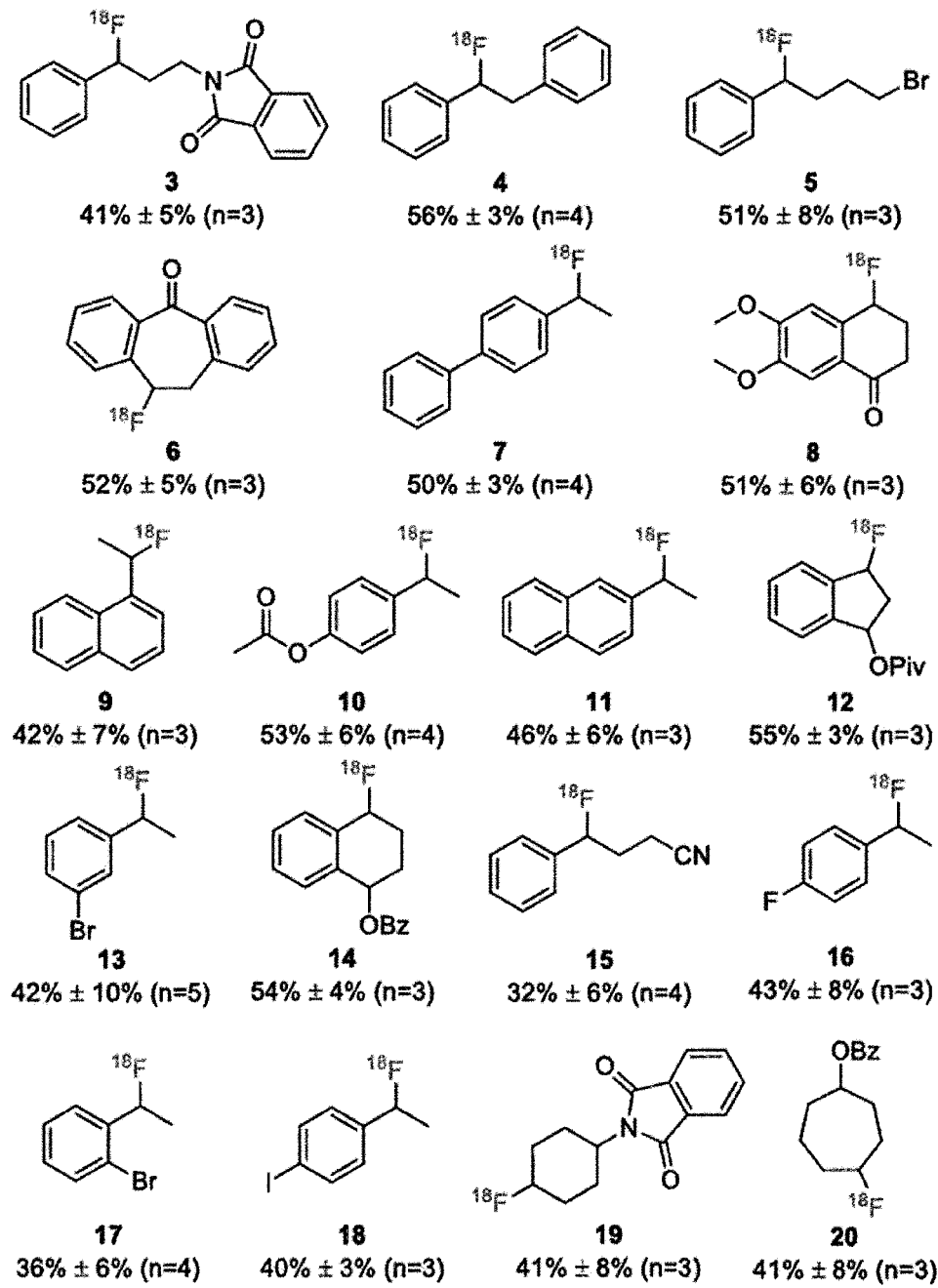
FIG. 6 illustrates [$^{18}$F] labeled compounds synthesized according to methods described herein.
Figure 7:
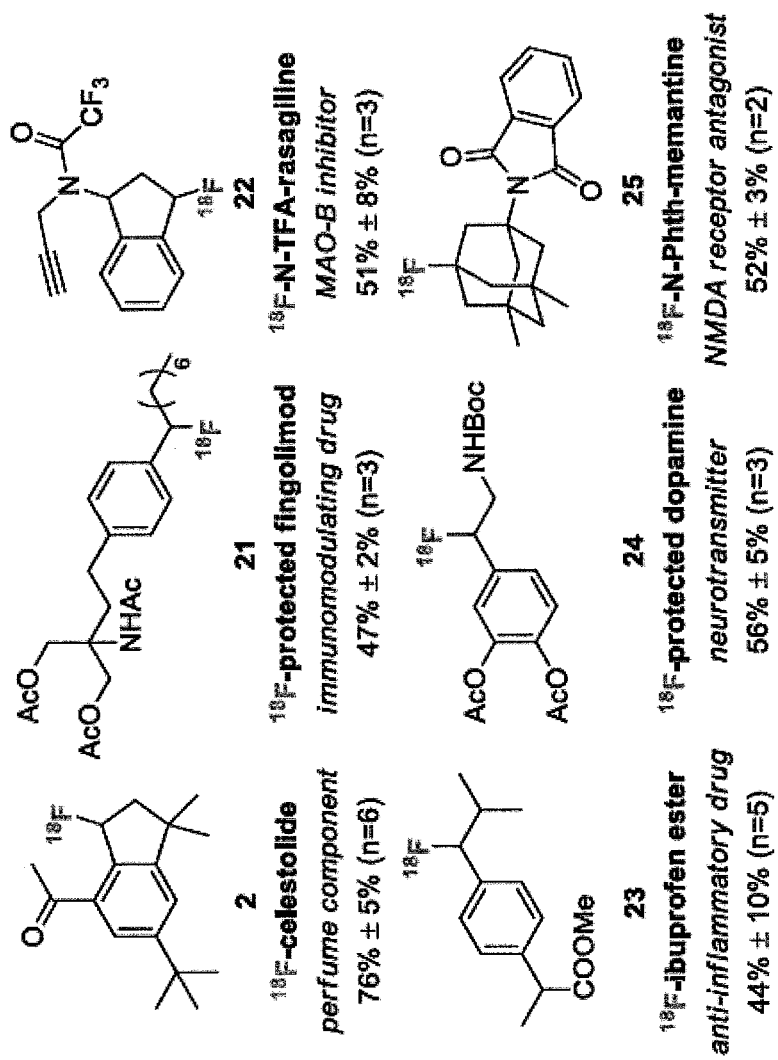
FIG. 7 illustrates [$^{18}$F] labeled bioactive compounds synthesized according to methods described herein.

Compounds 2-25 were prepared according to the reaction scheme of FIG. 5 and as follows. Compounds 2-25 are also illustrated in FIGS. 6 and 7.

General Information

Substrates of product 3, 12, 14, 19, 20, 22, 23, 24, 25 were purchased from commercial sources and were protected according to literature procedures. Mn(MCP)(OTf)$_2$, Fe(MCP)(OTf)$_2$ and Mn(PDP)(OTf)$_2$ were synthesized as previous described. 3-Chloroperbenzoic acid (m-CPBA) was purified using literature protocol. Substrate of product 21 was purchased from Matrix Scientific. Other commercial materials were of the highest purity available from Aldrich and used without further purification. $^1$H NMR spectra were obtained on a Bruker NB 300 spectrometer or a Bruker Avance-III (500 MHz) spectrometer and are reported in ppm using solvent as an internal standard (CDCl$_3$ at δ 7.26, acetone-d$_6$ at 2.04 or methylene chloride-d$_2$ at 5.32). Data reported as: chemical shift (δ), multiplicity (s=singlet, d=doublet, t=triplet, q=quartet, m=multiplet), coupling constant (Hz); integrated intensity. $^{13}$C NMR spectra were recorded on a Bruker 500 (125 MHz) spectrometer and are reported in ppm using solvents as an internal standard (CDCl$_3$ at 77.15 ppm, acetone-d$_6$ at 29.92 ppm or methylene chloride-d$_2$ at 54.0). $^{19}$F NMR spectra (282 MHz) were obtained on a Bruker NB 300 spectrometer and were referenced relative to CFCl$_3$. High-resolution mass spectra were obtained from the Princeton University mass spectrometer facility by electrospray ionization (ESI). High-performance liquid chromatography (HPLC) was performed on an Agilent 1100 series instrument with a binary pump and a diode array detector.

Radiochemistry

General Methods

No-carrier-added [$^{18}$F]fluoride was produced from water 97% enriched in $^{18}$O (ISOFLEX, USA) by the nuclear reaction $^{18}$O(p,n)$^{18}$F using a Siemens Eclipse HP cyclotron and a silver-bodied target at Massachusetts General Hospital Athinoula A. Martinos Center for Biomedical Imaging. The produced [$^{18}$F]fluoride in water was transferred from the cyclotron target by helium push.

Radiosynthesis of $^{18}$F Labeled Molecules

A 1.5 mL vial with a screw cap was charged with Mn(MCP)(OTf)$_2$ (6 mg, 0.01 mmol, 20 mol %), substrate (0.05 mmol) and a stir bar (2×5 mm). A portion of aqueous [$^{18}$F]fluoride solution (40-50 μL, 4-5 mCi) obtained from the cyclotron was loaded on to an Chromafix PS-HCO$_3$ IEX cartridge, which had been previously washed with 5.0 mg/mL K$_2$CO$_3$ in Milli-Q water followed by 5 mL of Milli-Q water. Then, the cartridge loaded with [$^{18}$F]fluoride was washed with 2 mL Milli-Q water and [$^{18}$F]fluoride was released from the cartridge using 1 mL of (80% acetone and 20% 5.0 mg/mL K$_2$CO$_3$ in Milli-Q water) solution. 20 μL of this [$^{18}$F]fluoride acetone solution was added to the vial containing the catalyst and the substrate. The resulting solution was stirred for 1 min at room temperature. After the resulting solution was stirred at room temperature for a minute, m-CPBA (9 mg, 0.05 mmol) in 0.1 mL acetone was slowly added into the solution in a few seconds. The vial was capped and the homogenous solution was stirred at room temperature in air for 10 minutes. After 10 min, an aliquot of the reaction mixture was taken and spotted on a silica gel TLC plate. The plate was developed in an appropriate eluent and scanned with a Bioscan AR-2000 Radio TLC Imaging Scanner.

Radio-HPLC Characterization of the $^{18}$F Labeled Products

All labeled molecules were characterized by comparing the radio-HPLC trace of the crude reaction mixture to the HPLC UV trace of the authentic reference sample with methods detailed below. Note: There is a time difference (Δt) between the radio-HPLC trace and the HPLC UV trace due to the delay volume between the diode array detector and the radioactivity detector (for 1.0 ml/min flow rate, Δt≈0.35 min).

Method A

HPLC column: Agilent Eclipse XDB-C18, 5 μm, 4.6×250 mm

Conditions: 3% CH$_3$CN/H$_2$O→95% CH$_3$CN/H$_2$O over 20 min, 1.0 mL/min

Method B

HPLC column: Agilent Eclipse XDB-C18, 5 μm, 4.6×250 mm

Conditions: 3% CH$_3$CN/H$_2$O→95% CH$_3$CN/H$_2$O over 25 min, 1.0 mL/min

Method C

HPLC column: Agilent Eclipse XDB-C18, 5 μm, 4.6×150 mm

Conditions: H$_2$O (0.1% TFA, A) and CH$_3$CN (0.1% TFA, B), 3%→5% B, 0-3 min; 5%→50% B, 3-6 min; 50%→95%, 6-9 min; 95% B, 9-19 min, 1.0 mL/min

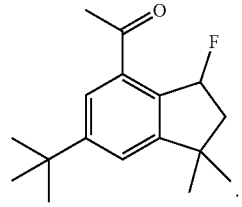

Compound 2

Purification by column chromatography (hexanes to 4% EtOAc/hexanes). $^1$H NMR (500 MHz, CDCl$_3$) 1.34 (s, 3H), 1.37 (s, 12H), 2.40-2.05 (m, 2H), 2.65 (s, 3H), 6.44 (ddd, J=54.0, 6.0, 1.5 Hz, 1H), 7.43 (t, J=1.5 Hz, 1H), 7.77 (d, J=1.7 Hz, 1H); $^{13}$C NMR (125 MHz, CDCl$_3$) δ 28.6, 29.0, 31.4, 31.5, 35.2, 42.7, 48.4, 94.0, 123.6, 125.8, 134.8, 135.1, 154.2, 155.8, 199.9; $^{19}$F NMR −158.6 ppm; MS (EI) m/z cal'd C$_{17}$H$_{23}$FO [M]$^+$: 262.2, found 262.2.

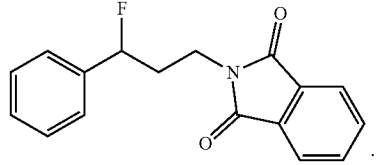

Compound 3

Purification by column chromatography (10% EtOAc/hexanes). $^1$H NMR (500 MHz, CDCl$_3$) δ 2.70-2.00 (m, 2H), 3.92 (td, J=7.2, 2.5 Hz, 2H), 5.57 (ddd, J=47.9, 8.6, 4.2 Hz, 1H), 7.46-7.30 (m, 5H), 7.80-7.67 (m, 2H), 7.85 (m, 2H); $^{13}$C NMR (125 MHz, CDCl$_3$) δ 34.6, 35.7, 92.6, 123.2, 125.6, 128.5, 128.7, 132.0, 134.1, 139.3, 168.3; $^{19}$F NMR −175.7 ppm; MS (EI) m/z cal'd C$_{17}$H$_{14}$FNO$_2$ [M]$^+$: 283.1, found 283.1.

Compound 4

Purification by flash chromatography (hexanes). $^1$H NMR (500 MHz, CDCl$_3$) δ 7.65-6.98 (m, 10H), 5.64 (ddd, J=47.1, 8.1, 5.0 Hz, 2H), 3.58-2.74 (m, 2H); $^{13}$C NMR (126 MHz, CDCl$_3$) δ 139.8, 136.8, 129.6, 126.8, 128.5, 125.8, 95.0 (d, J=174.3 Hz), 44.1 (d, J=24.3 Hz); $^{19}$F NMR −173.18 ppm; MS (EI) m/z cal'd C$_{14}$H$_{13}$F [M]$^+$: 200.1, found 200.1.

Compound 5

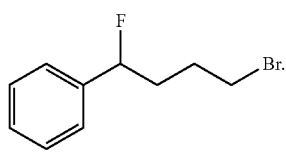

Purification by flash chromatography (hexanes) $^1$H NMR (500 MHz, CDCl$_3$) δ 7.43-7.36 (m, 2H), 7.36-7.31 (m, 2H), 5.48 (ddd, J=48.1, 8.0, 3.9 Hz, 1H), 3.59-3.31 (m, 2H), 2.19-1.87 (m, 4H); $^{13}$C NMR (125 MHz, CDCl$_3$) δ 139.8, 128.5, 125.4, 93.8 (d, J=171.5 Hz), 35.7, 33.4, 28.3; $^{19}$F NMR (282 MHz, CDCl$_3$) δ −176.03 ppm; MS (EI) m/z cal'd C$_{10}$H$_{12}$BrF [M]$^+$: 230.0, found 230.0.

Compound 6

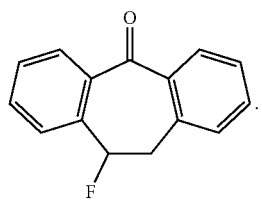

Purification by column chromatography (4% EtOAc/hexanes). $^1$H NMR (500 MHz, CDCl$_3$) δ 3.85-3.35 (m, 2H), 5.86 (ddd, J=47.7, 9.7, 2.0 Hz, 1H), 7.70-7.20 (m, 6H), 8.20-7.95 (m, 2H); $^{13}$C NMR (125 MHz, CDCl$_3$) δ 41.0, 90.5, 126.4, 127.5, 128.9, 130.2, 130.5, 130.6, 132.7, 132.8, 134.2, 136.2, 138.6, 139.2, 194.3; $^{19}$F NMR −168.8 ppm; MS (EI) m/z cal'd C$_{15}$H$_{11}$FO [M]$^+$: 226.1, found 226.1.

Compound 7

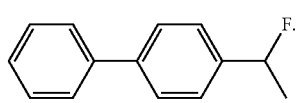

Purification by column chromatography (hexanes). $^1$H NMR (500 MHz, CDCl$_3$) δ 1.60 (dd, J=24.0, 6.4 Hz, 3H), 5.59 (dq, J=47.8, 6.4 Hz, 1H), 7.42-7.20 (m, 4H), 7.58-7.45 (m, 5H); $^{13}$C NMR (126 MHz, CDCl$_3$) δ 22.9, 90.8, 125.8, 127.1, 127.3, 127.5, 128.9, 140.7, 140.5, 141.3; $^{19}$F NMR −166.6 ppm; MS (EI) m/z cal'd C$_{14}$H$_{13}$F [M]$^+$: 200.1, found 200.1.

Compound 8

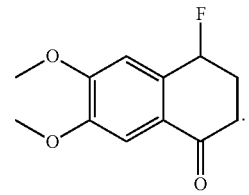

Purification by column chromatography (1%-20% EtOAc/hexanes). $^1$H NMR (500 MHz, CDCl$_3$) δ 2.53 (m, 3H), 3.00-2.85 (m, 1H), 3.95 (s, 3H), 4.00 (s, 3H), 5.70 (dt, J=51.0, 4.5 Hz, 1H), 7.00 (s, 1H), 7.54 (s, 1H); $^{13}$C NMR (125 MHz, CDCl$_3$) δ 30.0, 33.7, 56.2, 56.3, 88.2, 108.4, 109.5, 125.3, 135.0, 150.0, 154.0, 195.8; $^{19}$F NMR −169.6 ppm; MS (EI) m/z cal'd C$_{12}$H$_{14}$FO$_3$ [M+H]$^+$: 225.1, found 225.1.

Compound 9

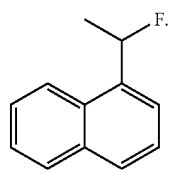

Purification by column chromatography (hexanes). $^1$H NMR (300 MHz, CDCl$_3$) δ 1.86 (dd, J=23.8, 6.4 Hz, 3H), 6.39 (dq, J=46.8, 6.5 Hz, 1H), 7.46-7.61 (m, 3H), 7.61-7.68 (m, 1H), 7.82-7.97 (m, 2H), 8.00-8.09 (m, 1H); $^{13}$C NMR (126 MHz, CDCl$_3$) δ 22.43 (d, J=25.1 Hz), 88.87 (d, J=167.6 Hz), 122.50 (d, J=10.0 Hz), 123.13 (d, J=1.3 Hz), 125.33, 125.71, 126.32, 128.77 (d, J=1.9 Hz), 128.90, 129.96 (d, J=3.5 Hz), 133.70, 136.98 (d, J=18.0 Hz); $^{19}$F NMR −169.8 ppm; MS (EI) m/z cal'd C$_{12}$H$_{11}$F [M]$^+$: 174.1, found 174.1.

Compound 10

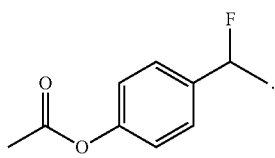

Purification by column chromatography (10% EtOAc/hexanes). $^1$H NMR (500 MHz, CDCl$_3$) δ 1.66 (dd, J=23.9, 6.4 Hz, 3H), 2.32 (s, 3H), 5.64 (dq, J=47.7, 6.4 Hz, 1H), 7.21-7.04 (m, 2H), 7.46-7.33 (m, 21-1); $^{13}$C NMR (125 MHz, CDCl$_3$) δ 21.5, 23.0, 90.4, 121.8, 126.5, 139.0, 150.5, 169.8; $^{19}$F NMR −166.4 ppm; MS (EI) m/z cal'd C$_{10}$H$_{11}$FO$_2$ [M]$^+$: 182.1, found 182.1.

Compound 11

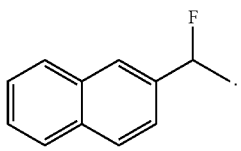

Purification by column chromatography (hexanes). $^1$H NMR (500 MHz, CDCl$_3$) δ 1.74 (dd, J=23.8, 6.5 Hz, 3H), 5.80 (dq, J=52.0, 6.3 Hz, 1H), 7.53-7.42 (m, 3H), 8.01-7.73 (m, 4H); $^{13}$C NMR (125 MHz, CDCl$_3$) δ 23.1, 91.3, 123.3, 124.2, 126.2, 127.7, 128.2, 128.4, 128.8, 133.0, 133.1, 138.9; $^{19}$F NMR −166.7 ppm; MS (EI) m/z cal'd C$_{12}$H$_{11}$F [M]$^+$: 174.1, found 174.1.

Compound 12

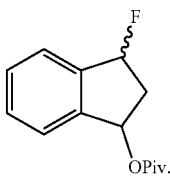

Purification by column chromatography (5% EtOAc/hexanes). Isolated as a single diastereomer. $^1$H NMR (500 MHz, CDCl$_3$) δ 1.23 (s, 9H), 2.38 (m, 1H), 2.84 (m, 1H), 6.15 (ddd, J=57.4, 6.4, 2.4 Hz, 1H), 6.42 (m, 1H), 7.51-7.37 (m, 3H), 7.55 (m, 1H); $^{13}$C NMR (126 MHz, CDCl$_3$) δ 27.1, 38.7, 40.6, 75.7, 94.4, 125.3, 125.7, 129.4, 130.5, 140.2, 142.4, 178.6; $^{19}$F NMR −164.1 ppm; MS (EI) m/z cal'd C$_{14}$H$_{17}$FO$_2$ [M]$^+$: 236.1, found 236.1.

Compound 13

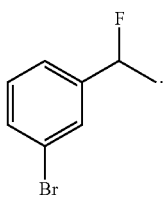

Purification by column chromatography (hexanes). $^1$H NMR (500 MHz, CDCl$_3$) δ 1.66 (dd, J=24.0, 6.4 Hz, 3H), 5.62 (dq, J=47.5, 6.4 Hz, 1H), 7.16-7.42 (m, 2H), 7.44-7.65 (m, 2H); $^{13}$C NMR (126 MHz, CDCl$_3$) δ 22.98, 90.04, 122.63, 123.79, 128.31, 130.19, 131.22, 143.84; $^{19}$F NMR (282 MHz, CDCl$_3$) −168.86 ppm; MS (EI) m/z cal'd C$_8$H$_8$BrF [M]$^+$: 202.0, found 202.0.

Compound 14

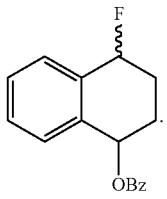

Purification by column chromatography (hexane to 10% EtOAc/hexanes). Two diastereomers 14a and 14b were separated as shown below.

Diastereomers 14a

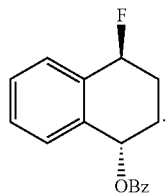

$^1$H NMR (500 MHz, CDCl$_3$) δ 2.33 (m, 4H), 5.68 (dt, J=51.2, 3.6 Hz, 1H), 6.33 (t, J=4.1 Hz, 1H), 7.48 (m, 7H), 8.04 (d, J=7.7 Hz, 2H); $^{13}$C NMR (126 MHz, CDCl$_3$) δ 166.01, 134.80, 134.28, 133.06, 130.34, 129.99, 129.93, 129.69, 129.66, 129.05, 128.37, 87.66, 69.35, 25.42, 24.20; $^{19}$F NMR (282 MHz, CDCl$_3$) δ −160.42 ppm; MS (EI) m/z cal'd C$_{17}$H$_{15}$FO$_2$ [M]$^+$: 270.1, found 270.1.

Diastereomers 14b

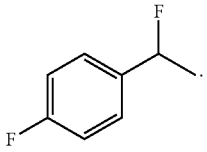

$^1$H NMR (500 MHz, CDCl$_3$) δ $^1$H NMR (500 MHz, CDCl$_3$) δ 2.31 (m, 4H), 5.62 (ddd, J=51.7, 6.3, 4.3 Hz, 1H), 6.23 (dd, J=7.1, 4.7 Hz, 1H), 7.49 (m, 7H), 8.12 (dd, J=8.2, 1.4 Hz, 1H); $^{13}$C NMR (126 MHz, CDCl$_3$) δ 166.32, 135.62, 134.88, 133.17, 130.18, 129.80, 129.36, 129.09, 128.58, 128.44, 128.10, 88.56, 70.27, 26.70, 26.53, 24.94; $^{19}$F NMR (282 MHz, CDCl$_3$) δ −161.24 ppm; MS (EI) m/z cal'd C$_{17}$H$_{15}$FO$_2$ [M]$^+$: 270.1, found 270.1.

Compound 15

Purification by chromatography (hexanes to 20% EtOAc/hexanes). $^1$H NMR (500 MHz, CDCl$_3$) δ 7.48-7.30 (m, 5H), 5.58 (ddd, J=47.6, 8.5, 4.1 Hz, 1H), 2.63-2.05 (m, 4H); $^{13}$C NMR (126 MHz, CDCl$_3$) δ 138.3, 129.1, 128.9, 125.4, 119.1, 92.1, 33.0, 13.5; $^{19}$F NMR (282 MHz, CDCl$_3$) −179.5 ppm; MS (EI) m/z cal'd C$_{10}$H$_{10}$FN [M]$^+$: 163.1, found 163.1.

Compound 16

Purification by column chromatography (hexanes). $^1$H NMR (500 MHz, CDCl$_3$) δ 1.66 (dd, J=23.8, 6.4 Hz, 3H), 5.63 (dq, J=47.5, 6.4 Hz, 1H), 7.13-7.04 (m, 2H), 7.36 (m, 2H); $^{13}$C NMR (126 MHz, CDCl$_3$) δ 22.9, 90.4, 115.4, 127.1, 162.6; $^{19}$F NMR –117.2, –166.0 ppm; MS (EI) m/z cal'd C$_8$H$_8$F$_2$ [M]$^+$: 142.1, found 142.1.

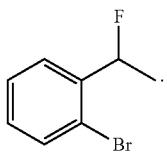

Compound 17

Purification by column chromatography (hexanes). $^1$H NMR (500 MHz, CDCl$_3$) δ 1.67 (dd, J=24.1, 6.4 Hz, 3H), 5.96 (dq, J=46.6, 6.4 Hz, 1H), 7.21 (td, J=7.8, 1.7 Hz, 1H), 7.41 (td, J=7.5, 1.2 Hz, 1H), 7.57 (dq, J=8.1, 1.5 Hz, 2H); $^{13}$C NMR (126 MHz, CDCl$_3$) δ 141.9, 133.6, 131.0, 129.1, 127.4, 121.2, 90.4, 22.3; $^{19}$F NMR –173.71 ppm; MS (EI) m/z cal'd C$_8$H$_8$BrF [M]$^+$: 202.0, found 202.0.

Compound 18

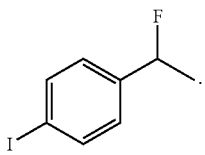

Purification by column chromatography (hexanes). $^1$H NMR (500 MHz, CDCl$_3$) δ 1.63 (dd, J=24.0, 6.4 Hz, 3H), 5.59 (dq, J=47.4, 6.4 Hz, 1H), 7.10-7.19 (m, 2H), 7.70-7.81 (m, 2H); $^{13}$C NMR (125 MHz, CDCl$_3$) δ 23.1, 90.5, 93.8, 127.3, 137.7, 141.3; $^{19}$F NMR –168.7 ppm; MS (EI) m/z cal'd C$_8$H$_8$FI [M]$^+$: 250.0, found 250.0.

Compound 19

Purification by column chromatography (5% EtOAc/hexanes). $^1$H NMR (300 MHz, CDCl$_3$) δ 1.48-1.80 (m, 4H), 2.15-2.31 (m, 2H), 2.67 (qd, J=13.4, 4.3 Hz, 21-1), 4.10-4.27 (m, 1H), 4.88 (d, J=48.1 Hz, 114), 7.79 (ddd, J=37.6, 5.5, 3.1 Hz, 414); $^{13}$C NMR (126 MHz, CDCl$_3$) δ 168.26, 133.87, 131.98, 123.13, 86.86, 49.65, 30.44, 23.89. $^{19}$F NMR (282 MHz, CDCl$_3$) δ –185.90 ppm; MS (EI) m/z cal'd C$_8$H$_8$FI [M]$^+$: 247.1, found 247.1.

Compound 20

The regiochemical assignment was made on the basis of three-bond F—C2 coupling, 26.48 ppm (d, J=8.1 Hz). $^1$H NMR (500 MHz, CDCl$_3$) δ 1.80-2.25 (m, 10H), 4.84 (m, 1H), 7.47 (2H), 7.54-7.63 (m, 1H), 8.02-8.11 (m, 2H); $^{13}$C NMR (126 MHz, CDCl$_3$) δ 17.66 (d, J=7.9 Hz), 26.48 (d, J=8.1 Hz), 28.55 (d, J=22.5 Hz), 34.04, 34.78 (d, J=22.0 Hz), 74.20, 92.87 (d, J=167.1 Hz), 128.34, 129.55, 130.69, 132.87, 165.86; $^{19}$F NMR (282 MHz, CDCl$_3$) δ –166.58 (m); MS (EI) m/z cal'd C$_8$H$_8$FI [M]$^+$: 236.1, found 236.1.

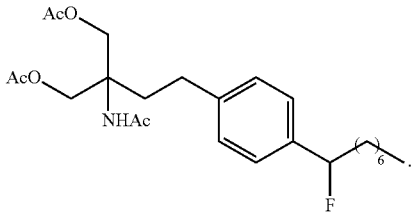

Compound 21

$^1$H NMR (500 MHz, Methylene Chloride-d$_2$) δ 0.91 (t, J=6.9 Hz, 3H), 1.22-1.54 (m, 10H), 1.97 (s, 3H), 2.10 (s, 6H), 2.12-2.25 (m, 4H), 2.57-2.72 (m, 2H), 4.35 (s, 4H), 5.46 (ddd, J=50, 8.1, 5.1 Hz, 1H), 5.70 (s, 1H), 7.22-7.30 (m, 4H); $^{13}$C NMR (126 MHz, Methylene Chloride-d$_2$) δ 13.85, 20.62, 22.63, 23.89 25.15 (d, J=4.5 Hz), 29.15, 29.26, 29.30, 31.76, 33.62, 37.01 (d, J=23.6 Hz), 57.96, 64.36, 94.67 (d, J=168.8 Hz), 125.84 (d, J=6.4 Hz), 128.35, 138.37 (d, J=19.8 Hz), 141.83, 169.89, 170.62; $^{19}$F NMR (282 MHz, CDCl$_3$) δ –167.49 (ddd, J=48.0, 27.6, 16.2 Hz) ppm; MS (EI) m/z cal'd C$_{25}$H$_{38}$FNO$_5$ [M]$^+$: 451.3, found 451.3.

Compound 22

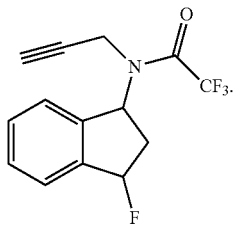

Purification by column chromatography (hexanes to 5% EtOAc/hexanes). Two diastereomers 22a and 22b were separated as shown below.

22a (containing two geometrical isomers in 2.8:1 ratio due to the amide moiety).

Major isomer: $^1$H NMR (500 MHz, methylene chloride-d2) δ 7.68-7.58 (m, 1H), 7.59-7.44 (m, 2H), 7.44-7.30 (m, 1H), 5.98 (ddd, J=57.5, 7.3, 3.5 Hz, 1H), 5.52 (td, J=7.8, 5.1 Hz, 1H), 5.36 (t, J=1.1 Hz, 1H), 4.02 (dd, J=17.2, 2.5 Hz, 1H), 3.74 (dd, J=17.2, 2.5 Hz, 1H), 3.18-2.99 (m, 1H), 2.66-2.47 (m, 1H), 2.23 (t, J=2.5 Hz, 1H); $^{13}$C NMR (126 MHz, methylene chloride-d2) δ 156.4, 140.6, 138.7, 130.8, 130.0, 126.0, 125.1, 116.6 (d, J=287.5), 92.9 (d, J=176.4 Hz), 78.6, 71.6, 59.5, 37.5, 32.9; $^{19}$F NMR (282 MHz, CDCl$_3$) δ −68.00 (s), −156.46 (dddd, J=57.7, 26.6, 16.2, 7.0 Hz); HRMS (ESI) m/z cal'd C$_{14}$H$_{11}$F$_4$NNaO [M+Na]$^+$: 308.0674, found 308.0670.

Minor isomer: $^1$H NMR (500 MHz, methylene chloride-d2) δ 7.63-7.59 (m, 1H), 7.52-7.48 (m, 2H), 7.38-7.34 (m, 1H), 6.07-6.01 (m, 1H), 5.97-5.94 (m, 1H), 4.22-4.13 (m, 1H), 3.99-3.92 (m, 1H), 3.05-2.97 (m, 1H), 2.71-2.60 (m, 1H), 2.32 (t, J=2.5 Hz, 1H); $^{13}$C NMR (126 MHz, methylene chloride-d2) δ 156.4, 141.1, 139.6, 130.5, 129.5, 125.8, 125.3, 115.6 (q, J=287.5), 93.5 (d, J=176.4 Hz), 78.7, 72.8, 58.1, 36.5, 33.5; $^{19}$F NMR (282 MHz, CDCl$_3$) δ −69.16 (s), −155.56.

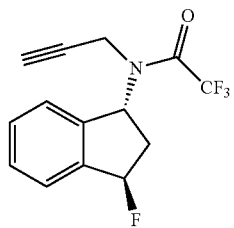

22b (containing two geometrical isomers in 2.3:1 ratio due to the amide moiety).

Major isomer: $^1$H NMR (500 MHz, Methylene Chloride-d$_2$) δ 2.31 (t, J=2.5 Hz, 1H), 2.78 (m, 2H), 3.45 (dd, J=17.4, 2.5 Hz, 1H), 4.12 (dd, J=17.4, 2.5 Hz, 1H), 5.96 (td, J=7.1, 3.5 Hz, 1H), 6.17 (m, 1H), 7.35 (d, J=7.4 Hz, 1H), 7.54 (m, 2H), 7.64 (dd, J=7.1, 2.0 Hz, 1H). $^{13}$C NMR (126 MHz, Methylene Chloride-d$_2$) δ 32.65, 38.17, 61.33, 71.84, 78.34, 93.76 (d, J=171.6 Hz), 116.50 (d, J=287.5 Hz), 124.54, 126.54, 129.81, 131.14, 140.04, 140.45, 156.81; $^{19}$F NMR (282 MHz, CDCl$_3$) δ −68.32, −160.81; HRMS (ESI) m/z cal'd C$_{14}$H$_{12}$F$_4$NO [M+H]$^+$: 286.0855, found 286.0858.

Minor isomer: $^1$H NMR (500 MHz, Methylene Chloride-d$_2$) δ 2.45 (t, J=2.5 Hz, 1H), 2.81 (m, 2H), 3.91 (m, 1H), 4.31 (dd, J=18.8, 2.4 Hz, 1H), 6.03 (td, J=7.6, 7.2, 3.2 Hz, 1H), 6.23 (ddd, J=55.1, 6.3, 2.1 Hz, 1H), 7.31 (d, J=7.0 Hz, 1H), 7.50 (m, 2H), 7.61 (m, 1H); $^{13}$C NMR (126 MHz, Methylene Chloride-d$_2$) δ 35.51, 37.27, 61.65, 73.24, 78.03, 94.77 (d, J=171.4 Hz), 114.00 (d, J=233.8 Hz), 124.27, 126.13, 129.22, 130.57, 140.17, 140.88, 157.10; $^{19}$F NMR (282 MHz, CDCl$_3$) −69.33, −162.23.

Compound 23

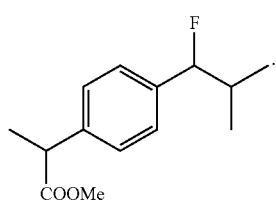

Purification by column chromatography (10% EtOAc/hexanes). $^1$H NMR (500 MHz, CDCl$_3$) 0.77 (d, J=7.0 Hz, 3H), 0.94 (d, J=6.8 Hz, 3H), 1.42 (dd, J=7.3, 4.5 Hz, 3H), 2.01 (dh, J=16.8, 6.7 Hz, 1H), 3.58 (s, 3H), 3.66 (q, J=7.2 Hz, 1H), 5.00 (dd, J=47.0, 6.7 Hz, 1H), 7.25-7.10 (m, 4H); $^{13}$C NMR (125 MHz, CDCl$_3$) δ 17.6, 18.4, 18.6, 34.2, 34.4, 45.1, 52.1, 99.2, 126.46, 126.52, 127.5, 138.5, 140.7, 175.1; $^{19}$F NMR −179.2 ppm; MS (EI) m/z cal'd C$_{14}$H$_{19}$FO$_2$ [M]$^+$: 238.1, found 238.1.

Compound 24

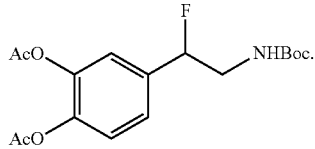

$^1$H NMR (500 MHz, acetone-d$_6$) δ 7.38-7.27 (m, 3H), 6.38 (br, 1H), 5.60 (ddd, J=47.6 7.6, 4.0 Hz, 1H), 3.58-3.44 (m, 2H), 2.29 (s, 3H), 2.28 (s, 3H), 1.43 (s, 9H); $^{13}$C NMR (126 MHz, acetone-d$_6$) δ 167.79, 167.78, 155.84, 142.65, 142.59, 136.60, 123.81, 123.70, 121.11, 91.96, 78.30, 45.94, 27.72, 19.67, 19.66; $^{19}$F NMR −182.20 ppm; MS (EI) m/z cal'd C$_{17}$H$_{23}$FNO$_6$ [M]$^+$: 355.1, found 355.1.

Compound 25

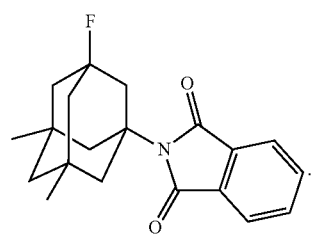

Purification by column chromatography (5% EtOAc/hexanes). $^1$H NMR (500 MHz, CDCl$_3$) δ 1.03 (s, 6H), 1.22 (m, 2H), 1.65 (m, 4H), 2.14 (m, 4H), 2.60 (d, J=6.2 Hz, 2H), 7.74 (m, 4H). $^{13}$C NMR (126 MHz, CDCl$_3$) δ 169.43, 133.90, 131.72, 122.73, 93.69, 62.44, 49.07, 47.56, 44.89, 43.83, 34.82, 29.22; $^{19}$F NMR (282 MHz, CDCl$_3$) δ −135.68 ppm; MS (EI) m/z cal'd C$_{20}$H$_{22}$FNO$_2$ [M]$^+$: 327.2, found 327.2.

Example 2 Formation and Characterization of [Mn(IV)(O)(Mcp)(L)]$^+$ Complex

Figure 8:
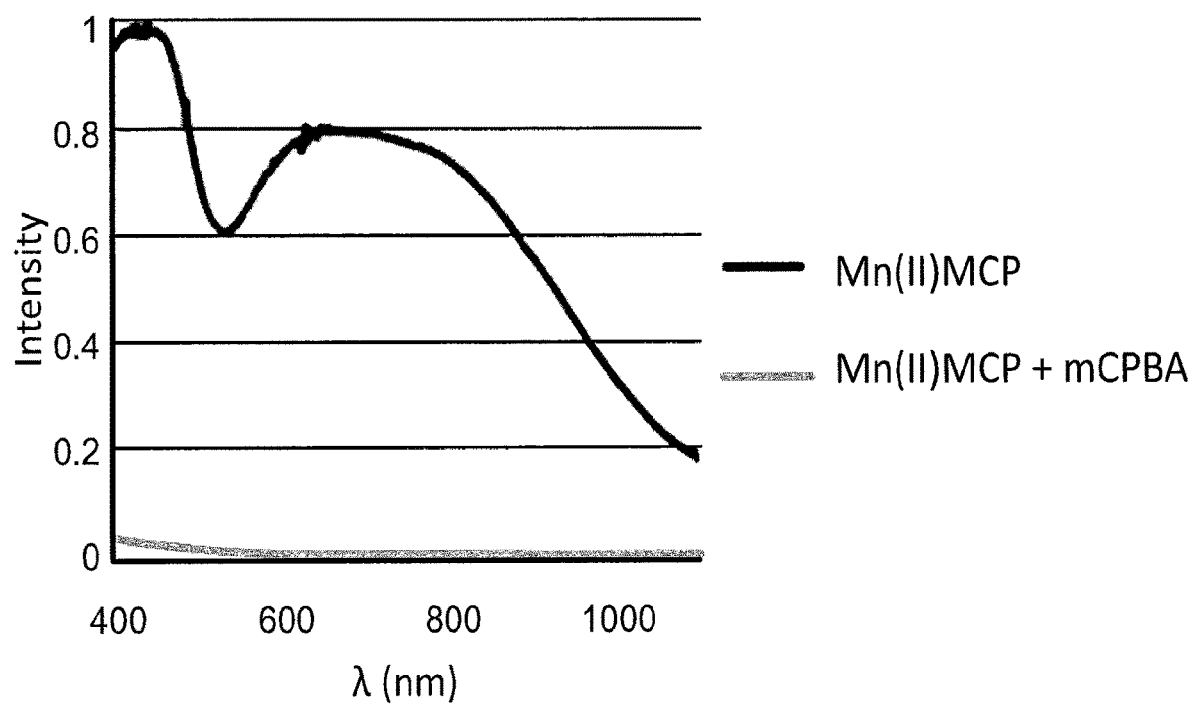
FIG. 8 are UV-vis spectra confirming formation of [Mn(IV)(O)(mcp)(L)]$^+$ complex according to one embodiment.
Figure 9:
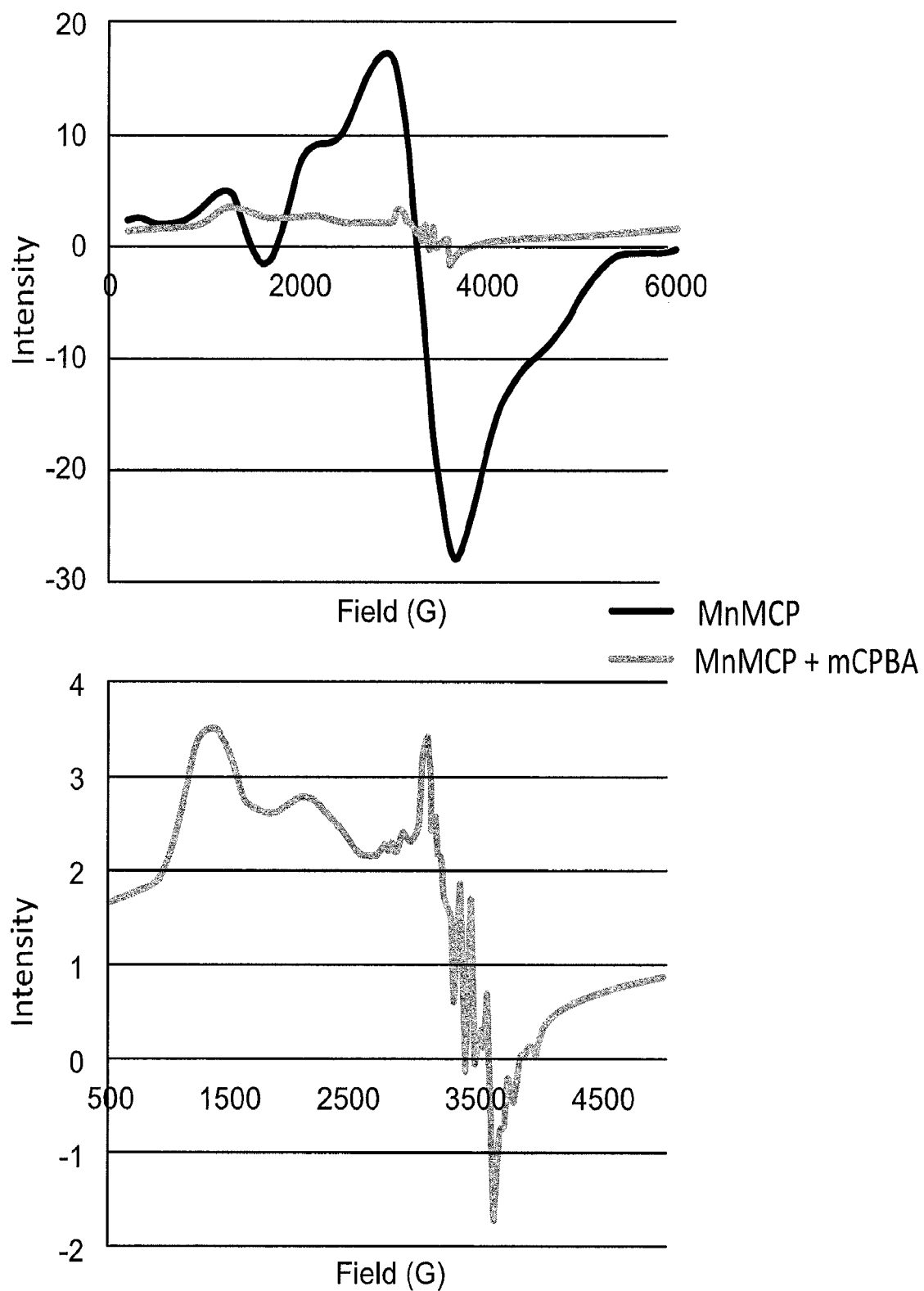
FIG. 9 are electron paramagnetic resonance (EPR) spectra confirming formation of [Mn(IV)(O)(mcp)(L)]$^+$ complex according to one embodiment.

[Mn(IV)(O)(mcp)(L)]$^+$ was prepared by treating Mn(II)(mcp)(CF$_3$SO$_3$)$_2$ with m-CPBA in CH$_3$CN at −30° C. Mn(II)(mcp)(CF$_3$SO$_3$)$_2$ (2 mg, 1 mM) dissolved in 3 mL of CH$_3$CN was stirring at −30° C. for 5 minutes. m-CPBA (2.6 mg, 5 equiv.) in 200 μL CH$_3$CN was added in one portion. Reaction was run under −30 C and UV-vis spectrum was used to monitor progress of reaction, showing the appearance of a new absorption at 751 nm as illustrated in FIG. 8. After the reaction was finished, the mixture was frozen by liquid N for measurement of electron paramagnetic resonance (EPR). All EPR were run at 5K using CH$_3$CN as solvent. When Mn(mcp)(CF$_3$SO$_3$)$_2$ was oxidized to [Mn(IV)(O)(mcp)(L)]$^+$, the EPR exhibits a characteristic rhombic Mn(IV) signal. In addition to characteristic Mn(IV) peak, a small amount of multiline was observed at g=2 region, which can be assigned as a small amount of Mn(II) species as illustrated in FIG. 9.

Example 3 Preparation of [Mn(II)(Mep)F$_2$](PF$_6$)

[Mn(II)(mep)F$_2$](PF$_6$) was prepared by treating mep ligand (N,N'-dimethyl-N,N'-bis-(2-pyridyl methyl)-ethane- 1,2-diamine) with stoichiometric amount of MnF$_3$. Typically, after mep (270 mg, 1 mmol) was dissolved in 10 mL 1:1 THF/MeOH, MnF (112 mg, 1 mmol) MnF$_3$ was added into the solution in solid form and the reaction mixture was stirred at room temperature for 30 minutes. Tetrabutylammonium hexafluorophosphate, NBu$_4$PF$_6$ (1.55 g, 4 mmol) saturated in THF was added into reaction mixture. The resulting solution was left without stirring until the crystallization was finished. The product was collected by filtration (416 mg, 82% yield).

Example 4 Reaction of t-Butyl 2-Phenylpropaneperoxoate with [Mn(II)(Mep)F$_7$](PF$_6$)

The thermal decomposition of t-butyl 2-phenylpropaneperoxoate was conducted at 105 C in the presence of a stoichiometric amount of [Mn(II)(mep)F$_2$](PF$_6$). Typically, a 4 mL vial with a screw cap was charged with [Mn(II)(mep)F$_2$](PF$_6$) (50.8 mg, 0.1 mmol) and t-butyl 2-phenylpropaneperoxoate (22.2 mg, 0.1 mmol) and a stir bar. The vial was evacuated and backfilled with N$_2$ for three times. Degassed CH CN (1 mL) was added into the vial via syringes, and the vial was sealed by parafilm. After the solution was heated at 105 C for 10 minutes, the vial was cooled to room temperature and the yield of 1-fluoroethyl benzene was determined by $^{19}$F NMR (δ −166.6 ppm) using 4-nitrofluorobenzene as the internal standard.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of fluorination comprising:
providing a reaction mixture including a non-heme manganese catalyst, a substrate comprising an sp$^3$ C—H bond and a fluorinating agent; and
converting the sp$^3$ C—H bond to a sp$^3$ C—F bond via transfer of fluorine to the substrate from a cis-F—Mn—OH species of the non-heme manganese catalyst, wherein the non-heme manganese catalyst is selected from the group consisting of Mn(mep)F$_2$, Mn(mcp)(OTf)$_2$, Mn(mcp)(OH)(F), Mn(mcp)(O)(F), Mn(pdp)(OTf)$_2$, Mn(pdp)(OH)(F), and Mn(pdp)(O)(F).

2. The method of claim 1, wherein the fluorinating agent comprises an $^{18}$F source to provide a sp$^3$ C-$^{18}$F bond.

3. The method of claim 2, wherein the $^{18}$F source is [$^{18}$F]F$^-$.

4. The method of claim 3, wherein the [$^{18}$F]F$^-$ is no carrier added.

5. The method of claim 2, wherein the sp$^3$ C—H bond is part of an alkyl moiety or cycloalkyl moiety.

6. The method of claim 5 having a radiochemical conversion greater than 50 percent.

7. The method of claim 1, wherein the substrate includes one or more aryl or heteroaryl moieties.

8. The method of claim 1, wherein the substrate includes one or more functionalities selected from the group consisting of ester, ether, ketone, cyanide, imide, aryl halide and alkyl halide.

9. The method of claim 1, wherein the reaction mixture further comprises an oxidant.

10. The method of claim 9, wherein the oxidant is soluble in solvent of the reaction mixture.

11. The method of claim 1, wherein the non-heme manganese catalyst is present in the reaction mixture in an amount of 1-30 mol %.

12. The method of claim 2 having a radiochemical conversion of at least 30 percent.

13. The method of claim 2 having a radiochemical conversion of at least 50 percent.

14. The method of claim 1, wherein solvent of the reaction mixture is acetone or acetonitrile.

15. The method of claim 1, wherein the substrate is a bioactive compound.

16. The method of claim 15, wherein the bioactive compound is selected from the group consisting of celestolide, protected fingolimod, N-TFA-rasagiline, ibuprofen ester, protected dopamine, N-Phth-amantadine and derivatives thereof.

17. The method of claim 1, wherein the reaction mixture is free of phase transfer catalyst.

18. A method of fluorination comprising:
providing a reaction mixture including a non-heme manganese catalyst, a substrate comprising an sp$^3$ C—H bond and a fluorinating agent; and
converting the sp$^3$ C—H bond to a sp$^3$ C—F bond via transfer of fluorine to the substrate from an equatorial ligand position on the non-heme manganese catalyst, wherein the reaction mixture is free of phase transfer catalyst, and the non-heme manganese catalyst is selected from the group consisting of Mn(mep)F$_2$, Mn(mcp)(OTf)$_2$, Mn(mcp)(OH)(F), Mn(mcp)(O)(F), Mn(pdp)(OTf)$_2$, Mn(pdp)(OH)(F), and Mn(pdp)(O)(F).

19. The method of claim 18, wherein the fluorinating agent comprises an $^{18}$F source to provide a sp$^3$ C-$^{18}$F bond.

20. The method of claim 19, wherein the $^{18}$F source is [$^{18}$F]F$^-$.

21. The method of claim 20, wherein the [$^{18}$F]F$^-$ is no carrier added.

22. The method of claim 20, wherein the sp$^3$ C—H bond is part of an alkyl moiety or cycloalkyl moiety.

23. The method of claim 22 having a radiochemical conversion greater than 50 percent.

24. The method of claim 18, wherein the substrate includes one or more aryl or heteroaryl moieties.

25. The method of claim 18, wherein the substrate includes one or more functionalities selected from the group consisting of ester, ether, ketone, cyanide, imide, aryl halide and alkyl halide.

* * * * *